(12) United States Patent
Park

(10) Patent No.: US 7,311,676 B2
(45) Date of Patent: Dec. 25, 2007

(54) PORTABLE NON-INVASIVE DEVICE FOR MEASURING THE HARDNESS OF MUSCLE OR MUSCLE COMPARTMENT

(76) Inventor: SangDo Park, 2101 Chestnut St. Apt. 607, Philadelphia, PA (US) 19103

( * ) Notice: Subject to any disclaimer, the term of this patent is extended or adjusted under 35 U.S.C. 154(b) by 0 days.

(21) Appl. No.: 11/232,758

(22) Filed: Sep. 23, 2005

(65) Prior Publication Data

US 2007/0073193 A1    Mar. 29, 2007

(51) Int. Cl.
*A61B 5/117* (2006.01)
*A61B 5/103* (2006.01)

(52) U.S. Cl. .................................... 600/587

(58) Field of Classification Search ............. 600/587, 600/591; 33/558.04, 784; 73/823; 30/90.7, 30/90.4, 90.9, 91.1, 91.2; 606/102, 206
See application file for complete search history.

(56) References Cited

U.S. PATENT DOCUMENTS

| | | | | |
|---|---|---|---|---|
| 2,845,704 A | * | 8/1958 | Huve | 30/90.7 |
| 3,008,239 A | * | 11/1961 | Lange | 33/558.04 |
| 4,159,640 A | | 7/1979 | Leveque | |
| 4,432,376 A | * | 2/1984 | Huszar | 600/587 |
| 4,817,629 A | | 4/1989 | Davis | |
| 5,038,795 A | | 8/1991 | Roush | |
| 5,997,545 A | * | 12/1999 | Doherty et al. | 606/102 |
| 6,063,044 A | | 5/2000 | Leonard | |
| 6,659,967 B1 | | 12/2003 | Steinberg | |

OTHER PUBLICATIONS

Steinberg, BD et al. "Evaluation of Limb Compartments with Suspected Increased Interstitial Pressure." Clincal Orthopaedics and Related Research. (300): 248-53, Mar. 1994.

* cited by examiner

*Primary Examiner*—Max F. Hindenburg
*Assistant Examiner*—Brian Szmal

(57) ABSTRACT

The device is a portable non-invasive device which uses purely mechanical components to measure the hardness of muscle or muscle compartment. It is comprised of two long members coupled rotationally in a scissor-like manner with the handles on one side of the hinge and the graspers on the other side. Built onto the device is a mechanism to modulate the extent of compression of the muscle via a calibrated block situated across the members so that a predetermined amount of compression of the muscle will occur as the distance between the handles is decreased manually by the operator. The force necessary to compress the muscle by the set predetermined amount is measured by the distention of the spring mechanism attached to the handle.

4 Claims, 1 Drawing Sheet

PORTABLE NON-INVASIVE DEVICE FOR MEASURING THE HARDNESS OF MUSCLE OR MUSCLE COMPARTMENT

REFERENCES CITED

U.S. Patent Documents

| | | |
|---|---|---|
| 3,696,662 | October 1972 | Foltz et al |
| 4,159,640 | July 1979 | Leveque et al |
| 4,817,629 | April 1989 | Davis et al |
| 5,038,795 | August 1991 | Roush et al |
| 6,063,044 | May 2000 | Leonard et al |
| 6,659,967 | December 2003 | Steinberg |

Other References

Steinberg, B D et al. "Evaluation of Limb Compartments with Suspected Increased Interstitial Pressure." *Clincal Orthopaedics and Related Research*. (300): 248-53, 1994 March.

BACKGROUND OF THE INVENTION

1. Technical Field

This invention is used to measure the hardness of muscle or muscle compartment through means of a portable and mechanically simple device that measures the force necessary to compress the muscle by a given amount. This is of relevance to the field of medicine dealing with musculoskeletal problems in which muscle hardness is directly related to muscle tone or abnormal process occurring within or around the muscle.

2. Description of the Prior Art

Muscles of the limb lie within compartments which are bound by fasciae. In the physical examination, the palpation of the muscle by the physician provides an important subjective data which lends crucial insight into the normal and abnormal processes occurring within the muscle or the muscle compartment. There are numerous neuromuscular conditions which manifest as palpable changes in muscle tone varying from flaccid hypotonia to spastic hypertonia. Moreover, there is a dangerous clinical entity known as compartment syndrome which manifests as increase in muscle hardness which if untreated can result in permanent disability and deformity. Although the tone of the muscle itself does not change with this syndrome, the increased pressure build-up in the interstitial tissue of the muscle compartment manifests as hardness which can be palpated in similar manner.

In current medical practice, there exists no device or means to measure the hardness of a patient's muscle or muscle compartment that is quick and easy to use in routine clinical setting. There are patents which assess human tissue hardness by means of apparatus having electronic components to measure force applied and/or distance displaced (Roush et al U.S. Pat. No. 5,038,795; Leveque U.S. Pat. No. 4,159,640; Leonard et al U.S. Pat. No. 6,063,044; Steinberg 6,659,967). However, the complexity associated with use, design, cost, and the increased number of components that can fail contributed to the reluctance of medical community in implementing the routine use of such devices for routine clinical purpose.

As mentioned above, diagnosing compartment syndrome is one application of a device which measures hardness of muscle. As shown in orthopedic literature by Steinberg (Steinberg 1994), increased intra-compartmental pressure manifests itself clinically by hardness of the muscle compartment which can then be measured non-invasively. But for the reasons iterated above, such device (Steinberg U.S. Pat. No. 6,659,967) is not part of routine clinical practice.

A device that is in current clinical practice for diagnosis of compartment syndrome is a needle and syringe pressure transducer system under the U.S. Pat. No. 4,817,629. This invasive device requires the needle to penetrate into the individual muscle compartments in question and is a direct measurement of each compartment pressure. Although it gives the only quantitative data in making the diagnosis (pain, hardness, decreased sensation, and decreased pulse comprise the subjective data), the obvious disadvantages of this method are numerous. For instance, the patients presenting with compartment syndrome of the leg or a suspected compartment syndrome already have exquisitely painful limbs which are further subject to the pain induced by introduction of the needle deeply into their muscle compartments at least four times (there are 4 compartments in the leg). Moreover, in cases of equivocal clinical findings, it is commonplace to perform repeat compartment measurements in order to monitor whether the symptoms will progress into frank compartments syndrome, and this leads to significant increase in pain and distress to the patient. There are also risks of injuring the arteries or nerves with this invasive technique which is not routinely performed under any imaging guidance. Also, microorganisms can be introduced into the deep compartments if meticulous aseptic techniques are not employed and result in infection. In addition, the physician is at risk of injuring him/herself with the needle especially if the patient does not hold still. Thus, a functional alternative to this invasive method is warranted.

BRIEF SUMMARY OF THE INVENTION

This invention seeks to provide a method to measure the hardness of a muscle or muscle compartment through the means of an inexpensive non-invasive device which is easy to build and use with very few components. Unlike the previous patents for measuring hardness of human tissue, the present invention measures only one variable, the force necessary to compress muscle by a set predetermined amount, without the use of any electronic or computer device. This portable device is comprised of two symmetrical long members coupled rotationally in a scissor-like manner and having the function of grasping around the muscle on one end and the function of handles and force measuring device at the other end so that bringing together the handles manually will approximate the grasping ends around muscle exerting compression onto it and the force necessary to do so can be measured. Built onto the device is a mechanism to modulate the extent of compression via a calibrated block/reciprocal block mechanism situated across the members so that a predetermined amount of compression of muscle will occur with bringing together of the handles. The force necessary to compress the muscle by the set predetermined amount is measured by a spring mechanism linked to the handle which measures the amount of distention of the spring as force. In order to accommodate muscles of different hardness, different springs with constants (k) can be interchangeably applied onto the apparatus.

BRIEF DESCRIPTION OF THE DRAWINGS

For a fuller understanding of the nature and objects of the invention, reference should be had to the following detailed description taken in conjunction with the accompanying drawings in which.

DETAILED DESCRIPTION OF THE PREFERRED EMBODIMENTS

Figure 1:
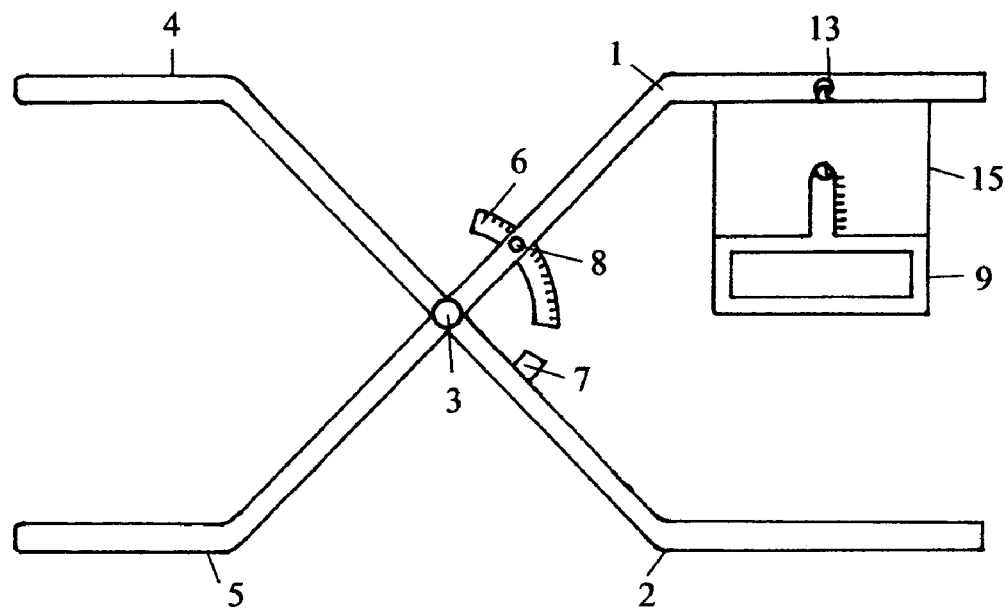
FIG. 1 is a plain view of one embodiment of the device.
Figure 2:
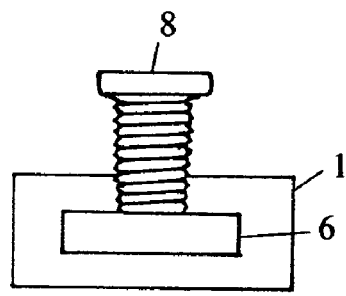
FIG. 2 is a cross sectional view of the calibrated block/reciprocal block mechanism.

A scissor-like device shown in FIG. 1 demonstrates symmetrical arms 1 and 2 made of sturdy material joined at a rotational hinge 3 so that motions at both sides of the hinge are coupled. The distance the two graspers 4 and 5 are allowed to travel toward each other, and hence the amount of compression of muscle, is controlled by the calibrated block/reciprocal block mechanism 6, 7, and 8 located on the opposite side of the hinge away from the graspers. The curve of the calibrated block 6/reciprocal block 7 is contoured so as to lie along the imaginary circle with the center of the circle being the hinge 3 and the radius of the circle being the distance of the calibrated block/reciprocal block from the hinge. This prevents interference with the motion of the arms 1 and 2. The calibrated block 6 and reciprocal block 7 lie in the same plane and their contact prevents further motion of the graspers 4 and 5 as the handle 9 and arm 2 are brought together. The reciprocal block 7 is connected to arm 2 and does not move. On the other hand, the calibrated block 6 fits in a slot within the body of arm 1 and is free to move along its length through this slot. Its position can be fixed by tightening of an adjusting screw 8 which exerts frictional compression of the calibrated block 6 against the slot wall. FIG. 2 is a cross sectional view of this scheme. The calibrated block 6 is engraved with lines each separated by a set amount to adjust for the amount of compression to be achieved.

Figure 3:
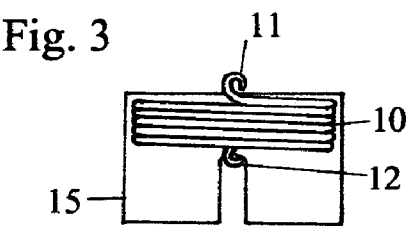
FIG. 3 is a view inside the spring mechanism.
Figure 4:
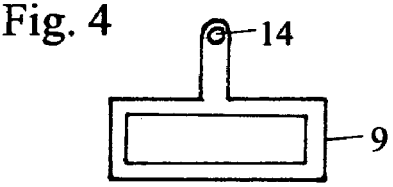
FIG. 4 is a view of the handle disassembled from the spring mechanism.

The spring mechanism is depicted in FIG. 3 and is comprised of a spring 10 with hooks 11 and 12 on both ends. Hook 11 allows for attachment to the hole 13 in arm 1, and hook 12 allows for attachment to the hole 14 in handle 9. The spring chamber 15 accommodates the distention of the spring 10. The force measurements engraved externally on the spring chamber are calibrated uniquely to the spring. Each line corresponds to the distance the spring is distended multiplied by the spring constant (k). The position of the bottom hook 12 of the spring attached to the hole 14 in handle 9 is read along these force measurement engravings on the exterior of spring chamber 15. Springs of different constant (k) and their spring chambers can be used interchangeably in this scheme to accommodate measurement of muscles of different hardness.

Example of Use in Regards to Compartment Syndrome

Anatomically, the portion of the leg which is below the knee and above the ankle is the most frequent site of compartment syndrome. Another common site is the portion of the arm below the elbow and above the wrist. Both regions have subcutaneous bones (tibia for the leg and ulna for the arm) which are easily palpable by touch directly beneath the skin with minimal fatty tissue interposition regardless of a person's body habitus. Grasper 4 is to be placed directly onto the skin directly overlying this subcutaneous bone while grasper 5 is to be placed directly onto the skin overlying one of the muscles of the compartment without compressing it. The calibrated block/reciprocal block mechanism screw 8 is loosened to slide the calibrated block 6 to make contact with the reciprocal block 7. The examiner then notes the specific line on the calibration block 6 using arm 1 as a reference and moves the calibrated block 6 away from the reciprocal block 7 a desired distance using the engraved lines as the guide and then tightens the adjusting screw 8. The examiner, with either one or both hands, brings together the handle 9 toward arm 2, and the position of the bottom hook 12 along the exterior of the spring chamber 15 is read as the calibrated block 6 makes contact with the reciprocal block 7 and prevents further compression of the muscle. This is the force necessary to compress the muscle in the compartment by an amount predetermined by the examiner using the calibration block/reciprocal block.

Thus a simple device and method for measuring hardness of muscle or muscle compartment has been shown and described above. It will be apparent that many changes, modifications, variations, and other uses and applications are possible and contemplated, and all such changes, modifications, variations, and other uses and applications which do not depart from the spirit and scope of the invention are deemed to be covered by the invention as is described in the Claims section.

I claim:

1. A device which non-invasively measures the hardness of a muscle or muscle compartment comprising:
   a. members which compress the muscle or muscle compartment as the members are brought toward each other; and
   b. a mechanism to variably set the amount of compression to be desired; and
   c. a coiled spring or plurality of coiled springs which measures a force necessary to achieve the desired amount of compression.

2. The device as claimed in claim 1, wherein the mechanism which variably sets the amount of compression comprises:
   a. a block situated in a slot within one of the members;
   b. the block moves within the slot in order to adjust the extent of the compression; wherein the extent of the compression is determinable by identifiable marks on the block, each mark representing a certain amount of compression;
   c. the block is fixable in a position by a means that exerts compression and friction on the block; and
   d. a reciprocal block situated on an opposite member across from the said block so that contact of the block with the reciprocal block occurs as the distance between the members is decreased.

3. The device as claimed in claim 1, wherein the coiled spring or plurality of coiled springs is linked to a handle and is further linked to a first arm wherein compression of the handle and a second opposing arm distends the coiled spring or plurality of coiled springs and the amount of distention corresponds to the measured force.

4. The device as claimed in claim 1, wherein different coiled springs with different spring constants (k) can be applied to accommodate muscles or muscle compartments of different hardnesses.

* * * * *